United States Patent
Iketani et al.

(10) Patent No.: US 12,198,235 B2
(45) Date of Patent: Jan. 14, 2025

(54) ENDOSCOPE SYSTEM, MEDICAL IMAGE PROCESSING DEVICE, AND OPERATION METHOD THEREFOR

(71) Applicant: FUJIFILM Corporation, Tokyo (JP)

(72) Inventors: Minoru Iketani, Kanagawa (JP); Tetsuya Fujikura, Kanagawa (JP); Haruo Akiba, Kanagawa (JP); Manabu Miyamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 228 days.

(21) Appl. No.: 17/809,235

(22) Filed: Jun. 27, 2022

(65) Prior Publication Data
US 2022/0414956 A1    Dec. 29, 2022

(30) Foreign Application Priority Data
Jun. 29, 2021 (JP) .................. 2021-108148

(51) Int. Cl.
*G06T 11/20* (2006.01)
*A61B 1/00* (2006.01)
(Continued)

(52) U.S. Cl.
CPC .......... *G06T 11/203* (2013.01); *A61B 1/0005* (2013.01); *G06T 7/0012* (2013.01);
(Continued)

(58) Field of Classification Search
CPC ....... G06T 11/203; G06T 7/0012; G06T 7/20; G06T 2207/10068; G06T 2207/30096;
(Continued)

(56) References Cited

U.S. PATENT DOCUMENTS

| | | |
|---|---|---|
| 2005/0215854 A1 | 9/2005 | Ozaki et al. |
| 2012/0209108 A1* | 8/2012 | Qian ............ A61B 6/037 600/425 |

(Continued)

FOREIGN PATENT DOCUMENTS

| | | |
|---|---|---|
| JP | 2005-278888 A | 10/2005 |
| JP | 2009-066301 A | 4/2009 |

(Continued)

OTHER PUBLICATIONS

The extended European search report issued by the European Patent Office on Nov. 4, 2022, which corresponds to European Patent Application No. 22181680.4-1126 and is related to U.S. Appl. No. 17/809,235.

(Continued)

*Primary Examiner* — Chong Wu
(74) *Attorney, Agent, or Firm* — Studebaker & Brackett PC

(57) ABSTRACT

The medical image processing device includes a processor, in which the processor acquires a medical image obtained by imaging a subject with an endoscope, identifies a tumor region and a non-tumor region from the medical image, generates a demarcation line that is a boundary between the tumor region and the non-tumor region, generates a virtual incision line at a position separated from the demarcation line by a designated distance, and performs control for superimposing the demarcation line and the virtual incision line on the medical image to be displayed.

15 Claims, 14 Drawing Sheets

(51) Int. Cl.
*G06T 7/00* (2017.01)
*G06T 7/20* (2017.01)
*G06V 10/22* (2022.01)

(52) U.S. Cl.
CPC .............. *G06T 7/20* (2013.01); *G06V 10/225* (2022.01); *G06T 2207/10068* (2013.01); *G06T 2207/30096* (2013.01); *G06V 2201/03* (2022.01)

(58) Field of Classification Search
CPC ........... G06T 7/11; G06T 7/12; A61B 1/0005; A61B 1/0004; A61B 1/000094; A61B 1/04; A61B 1/00009; A61B 1/00186; A61B 1/00188; A61B 1/0051; A61B 1/06; A61B 17/320016; A61B 90/361; G06V 10/225; G06V 2201/03
See application file for complete search history.

(56) References Cited

U.S. PATENT DOCUMENTS

| | | |
|---|---|---|
| 2012/0289801 A1 | 11/2012 | Yamaguchi |
| 2013/0258080 A1 | 10/2013 | Kuriyama |
| 2014/0334698 A1 | 11/2014 | Tanaka et al. |
| 2014/0363063 A1 | 12/2014 | Hendriks et al. |
| 2015/0031990 A1 | 1/2015 | Boctor et al. |
| 2015/0374452 A1 | 12/2015 | Saito |
| 2016/0143515 A1 | 5/2016 | Shimamoto et al. |
| 2016/0345834 A1 | 12/2016 | Hasan et al. |
| 2020/0297422 A1 | 9/2020 | Gocho et al. |
| 2021/0204794 A1 | 7/2021 | Yumbe |

FOREIGN PATENT DOCUMENTS

| | | |
|---|---|---|
| JP | 2012-115554 A | 6/2012 |
| JP | 2012-135476 A | 7/2012 |
| JP | 2015-504737 A | 2/2015 |
| JP | 2016-027367 A | 2/2016 |
| WO | 2014/188718 A1 | 11/2014 |
| WO | 2020/066941 A1 | 4/2020 |

OTHER PUBLICATIONS

Luo Huoling et al., "Augmented reality navigation for liver resection with a stereoscopic laparoscope," Computer Methods and Programs in Biomedicine, vol. 187, Oct. 7, 2019, 13 pages total, DOI: 10.1016/J.CMPB.2019.105099.

Communication pursuant to Article 94(3) EPC issued by the European Patent Office on Jul. 9, 2024, which corresponds to European Patent Application No. 22181680.4-1122 and is related to U.S. Appl. No. 17/809,235.

An Office Action; "Notice of Reasons for Refusal," mailed by the Japanese Patent Office on Oct. 22, 2024, which corresponds to Japanese Patent Application No. 2021-108148 and is related to U.S. Appl. No. 17/809,235; with English language translation.

* cited by examiner

ENDOSCOPE SYSTEM, MEDICAL IMAGE PROCESSING DEVICE, AND OPERATION METHOD THEREFOR

CROSS-REFERENCE TO RELATED APPLICATIONS

This application claims priority under 35 U.S.C § 119(a) to Japanese Patent Application No. 2021-108148 filed on 29 Jun. 2021. The above application is hereby expressly incorporated by reference, in its entirety, into the present application.

BACKGROUND OF THE INVENTION

1. Field of the Invention

The present invention relates to an endoscope system, a medical image processing device, and an operation method therefor capable of supporting an operation such as endoscopic submucosal dissection.

2. Description of the Related Art

Endoscopic submucosal dissection (ESD) makes it possible to resect tumors or the like with a size to which endoscopic mucosal resection (EMR) cannot be applied and thus to complete an operation without selecting a highly invasive surgery. ESD is performed endoscopically, and thus has the advantage of being minimally invasive. On the other hand, the gastrointestinal tract is extremely thin, 5 to 7 mm thick in the stomach and 3 to 5 mm thick in the large intestine, and advanced techniques are required for doctors who perform ESD.

There is a technique capable of showing a part to be resected to assist an operator during an operation. For example, there is a technique in which an operator is allowed to visually recognize a cutting position by superimposing a fluorescence image of a subject into which ICG is administered such that a portion scheduled to be removed emits fluorescence in order to remove an area of the Quino classification of the liver on an image that is captured after irradiating a subject with laser light serving as a cutting auxiliary line at a position separated by a cutting margin width from an affected part, computed from the fluorescence image (JP2016-27367A, corresponding to US2015/0374452A1).

There is a technique of irradiating an affected part with light for imaging and designating a designation region to be treated through spiral scanning in a case of performing ESD by using laser ablation for applying therapeutic laser (WO2014/188718A, corresponding to US2016/0143515A1).

SUMMARY OF THE INVENTION

In small clinics or operating rooms, it is preferable to secure leads and make an endoscope system as small as possible so as not to overwhelm a space. Therefore, it is necessary that an endoscope system does not require large-scale members such as a plurality of light source devices or cameras. There is a need for a technique for supporting an operator and performing safe and stable ESD in which the entire endoscope system is fitted in a compact size without using laser light for a cutting auxiliary line as disclosed in JP2016-27367A and a non-tumor region is preserved while appropriately resecting a tumor region.

The present invention provides an endoscope system, a medical image processing device, and an operation method therefor capable of simultaneously recognizing a lesion and a portion to be treated without using a special device.

According to an aspect of the present invention, there is provided a medical image processing device including a processor, in which the processor acquires a medical image obtained by imaging a subject with an endoscope, identifies a tumor region and a non-tumor region from the medical image, generates a demarcation line that is a boundary between the tumor region and the non-tumor region, generates a virtual incision line at a position separated from the demarcation line by a designated distance, and performs control for superimposing the demarcation line and the virtual incision line on the medical image to be displayed.

The processor preferably determines the virtual incision line as a determined incision line in a case where an approval instruction is given.

It is preferable that the processor changes a display position of the determined incision line in tracking of the tumor region in a case where the tumor region is moved on the medical image.

It is preferable that the processor sets a landmark on a determined incision line image in which the determined incision line is superimposed on the medical image, records the determined incision line and the landmark on the determined incision line image in association with each other, and changes the display position of the determined incision line according to movement of the landmark on the determined incision line image.

The display position of the determined incision line is preferably changed according to a change of an amount of gas. The display position of the determined incision line is preferably changed according to a change of an observation magnification of the medical image. A display mode of the determined incision line is preferably changed according to a bend of a mucous membrane on the medical image.

It is preferable that the tumor region includes a first tumor portion and a second tumor portion, the first tumor portion is displayed in a first medical image, and the second tumor portion is displayed to be included in a second medical image of which an imaging position is different from that of the first medical image, and in a case where a part of a first determined incision line corresponding to the first tumor portion and the virtual incision line corresponding to the second tumor portion are displayed as the determined incision line in a second display image corresponding to the second medical image, and there is an approval instruction for determining the virtual incision line corresponding to the second tumor portion as a second determined incision line, the processor updates the determined incision line by connecting the first determined incision line to the second determined incision line.

It is preferable that, in a case where the determined incision line includes a first tumor determined incision line corresponding to a first tumor region and a second tumor determined incision line corresponding to a second tumor region different from the first tumor region, and an overlapping region occurs in which a first region surrounded by the first tumor determined incision line and a second region surrounded by the second tumor determined incision line overlap each other, the processor generates a combined incision line by combining the first tumor determined incision line surrounding the first region excluding the overlapping region with the second tumor determined incision line surrounding the second region excluding the overlapping region.

The processor preferably sets the overlapping region as an incision impossible region. It is preferable that the processor recognizes a distance measurement index from the medical image and generates the demarcation line and the virtual incision line. It is preferable that the designated distance is freely settable. The subject is preferably a luminal organ.

According to another aspect of the present invention, there is provided an operation method for a medical image processing device, including a step of acquiring a medical image obtained by imaging a subject with an endoscope; a step of identifying a tumor region and a non-tumor region from the medical image; a step of generating a demarcation line that is a boundary between the tumor region and the non-tumor region; a step of generating a virtual incision line at a position separated from the demarcation line by a designated distance; and a step of performing control for superimposing the demarcation line and the virtual incision line on the medical image to be displayed.

According to still another aspect of the present invention, there is provided an endoscope system including the medical image processing device and the endoscope.

According to the present invention, a lesion and a portion to be treated can be simultaneously recognized without using a special device.

DESCRIPTION OF THE PREFERRED EMBODIMENTS

Figure 1:
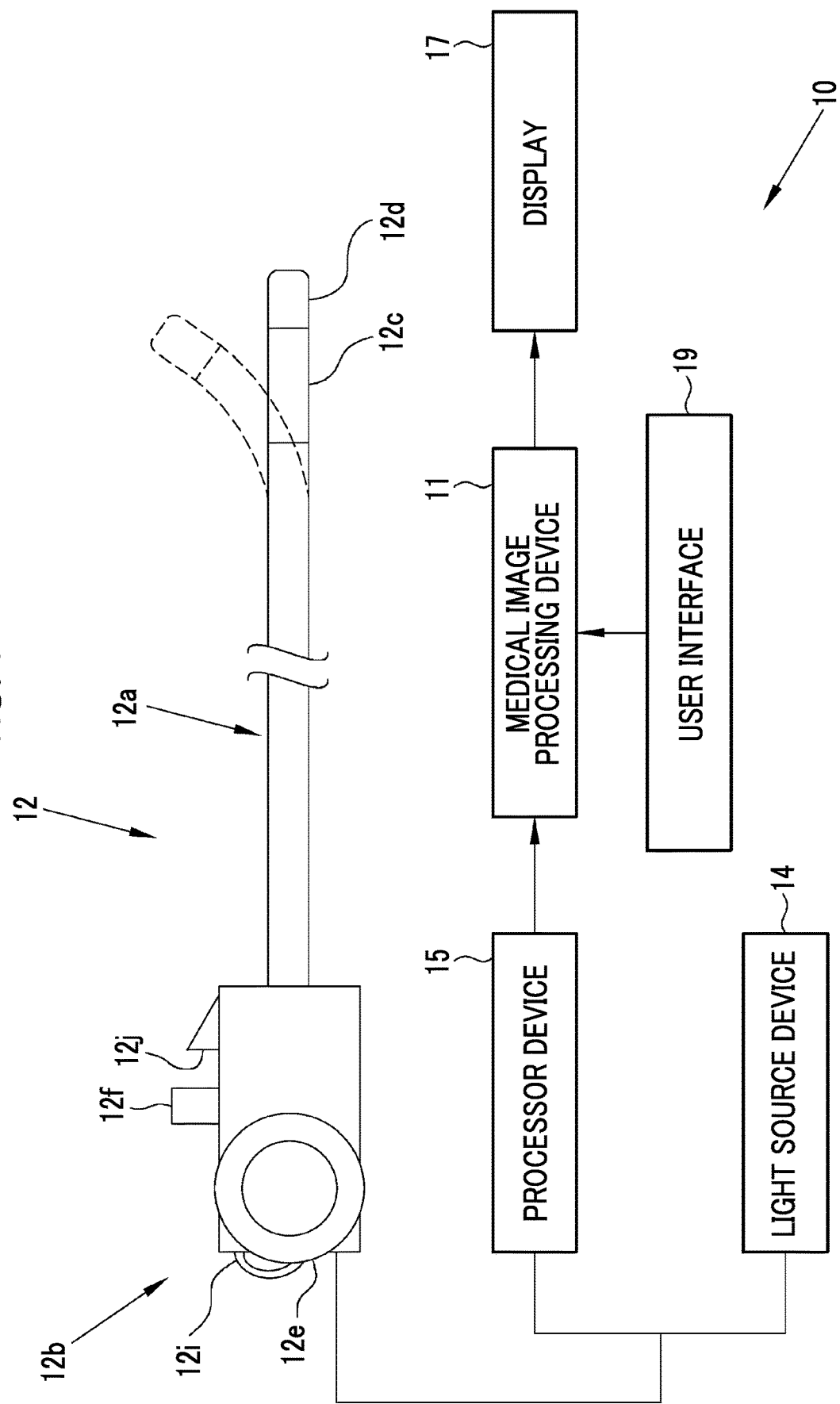
FIG. 1 is an explanatory diagram of a configuration of an endoscope system.

As shown in FIG. 1, an endoscope system 10 includes an endoscope 12, a light source device 14, a processor device 15, a medical image processing device 11, a display 17, and a user interface 19. The medical image processing device 11 is connected to the endoscope system 10 via the processor device 15. The endoscope 12 is optically connected to the light source device 14 and electrically connected to the processor device 15.

The endoscope 12 is provided on an insertion part 12*a* to be inserted into the body of an observation target, an operating part 12*b* provided at a base end portion of the insertion part 12*a*, and a bendable part 12*c* and a tip part 12*d* provided at a distal end side of the insertion part 12*a*. The bendable part 12*c* is bent by operating an angle knob 12*e* of the operating part 12*b*. The tip part 12*d* is directed in a desired direction in a case where the bendable part 12*c* is bent. A forceps channel (not shown) for inserting a treatment tool or the like is provided from the insertion part 12*a* to the tip part 12*d*. The treatment tool is inserted into the forceps channel from a forceps port 12*j*.

Inside the endoscope 12, an optical system for forming a subject image and an optical system for irradiating a subject with illumination light are provided. The operating part 12*b* is provided with an angle knob 12*e*, a mode selector switch 12*f*, a still image acquisition instruction switch 12*h*, and a zoom operating part 12*i*. The mode selector switch 12*f* is used for an observation mode selection operation. The zoom operating part 12*i* is used to operate a zoom lens 42.

The light source device 14 generates illumination light. The display 17 outputs and displays a medical image and an image in which a demarcation line and a virtual incision line or a determined incision line that will be described later are superimposed on the medical image. The user interface 19 has a keyboard, a mouse, a touch pad, a microphone, and the like, and has a function of receiving input operations such as function settings. The processor device 15 performs system control on the endoscope system 10 and image processing and the like on an image signal transmitted from the endoscope 12.

Figure 2:
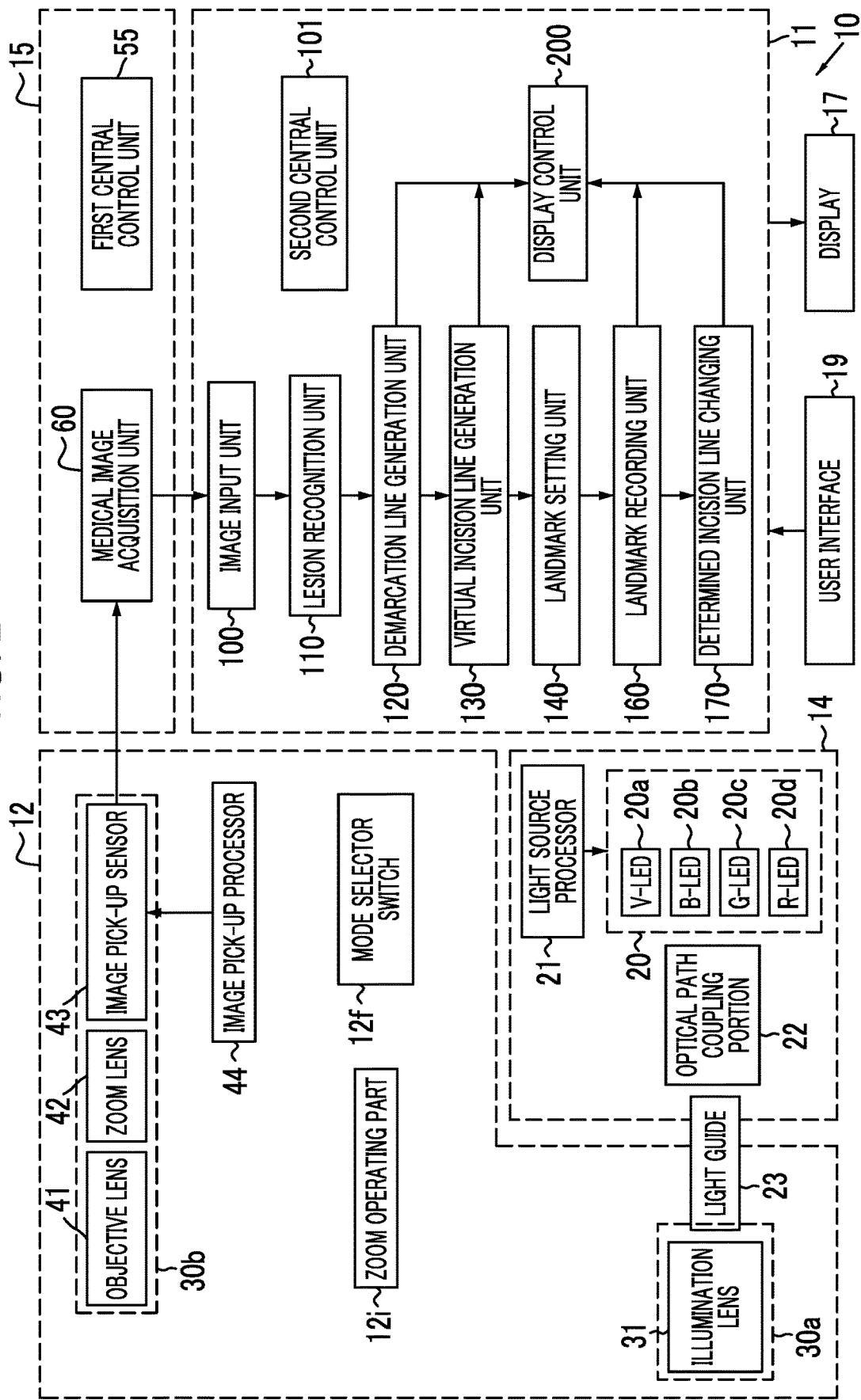
FIG. 2 is a block diagram showing a function of the endoscope system.

In FIG. 2, the light source device 14 includes a light source unit 20 and a light source processor 21 that controls the light source unit 20. The light source unit 20 has, for example, a plurality of semiconductor light sources, each of which is turned on or off, and in a case where the light source unit 20 is turned on, a light emission amount of each semiconductor light source is controlled such that illumination light for illuminating an observation target is emitted. The light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d. The light source unit 20 may be built in the endoscope 12, and the light source control unit may be built in the endoscope 12, or may be built in the processor device 15.

Figure 3:
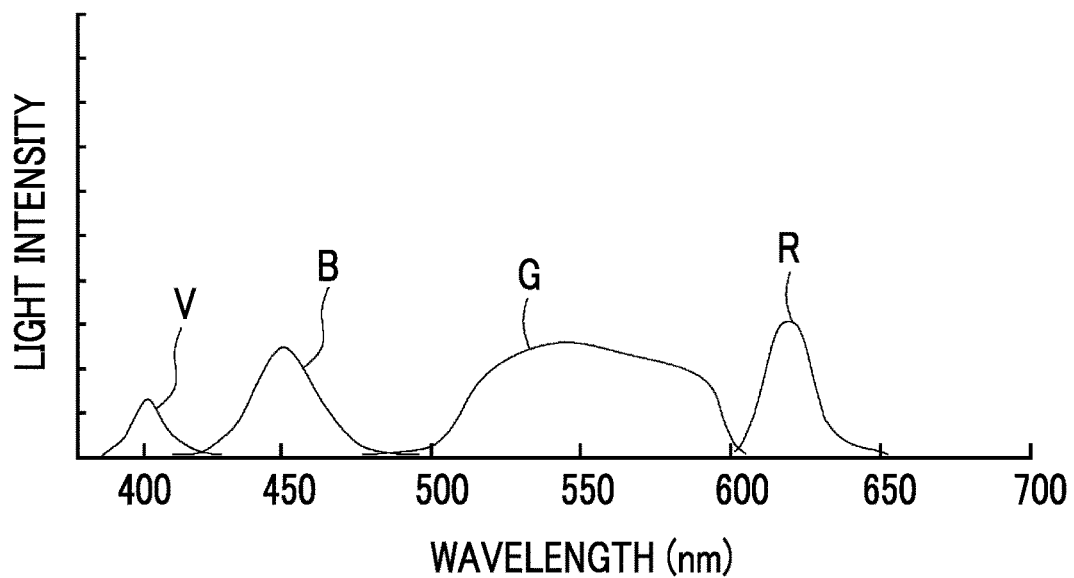
FIG. 3 is a graph showing spectra of violet light V, blue light B, green light G, and red light R.

In a case where the light source unit 20 emits normal light used for observing the entire observation target by giving brightness to the entire observation target, the light source unit 20 emits light having a spectrum as shown in FIG. 3. In this case, the V-LED 20a generates violet light V having a central wavelength of 405±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

The endoscope system 10 includes a mono-emission mode, a multi-emission mode, and an incision line display mode, which are be switched by the mode selector switch 12f. The mono-emission mode is a mode in which illumination light having the same spectrum is continuously applied to illuminate an observation target. The multi-emission mode is a mode in which a plurality of illumination light beams having different spectra are applied while being switched therebetween according to a specific pattern to illuminate an observation target. The illumination light includes normal light (broadband light such as white light) or special light used for emphasizing a specific region of an observation target. In the mono-emission mode, switching to illumination light having another spectrum may be performed by operating the mode selector switch 12f. For example, first illumination light and second illumination light having different spectra may be switched.

The incision line display mode is a mode for supporting incision of the mucous membrane in ESD by, in a case where the tumor is found in a subject, identifying a tumor region and a non-tumor region, generating a display image showing an operator a boundary line between the tumor region and the non-tumor region and a line at which the incision is actually performed, and displaying the display image on the display 17.

The light source processor 21 independently controls amounts of light of four colors such as the violet light V, the blue light B, the green light G, and the red light R. In the case of the mono-emission mode, illumination light having the same spectrum is continuously emitted for each frame. In the first illumination observation mode, a first illumination light image having a natural color is displayed on the display 17 by causing normal light such as white light (first illumination light) to illuminate an observation target and picking up an image thereof. The first illumination light and the second illumination light may be switched in the mono-emission mode, and a second illumination light image emphasizing a specific structure is displayed on the display 17 by causing special light (second illumination light) to illuminate an observation target and picking up an image thereof. The first illumination light image and the second illumination light image are a kind of medical image.

Light used for performing ESD is usually the first illumination light. In a case where it is desired to check an infiltration range of a lesion part before performing ESD, the second illumination light may be used. In the incision line display mode, it may be selected whether a medical image is obtained according to a light emission pattern in either the mono-emission mode or the multi-emission mode, or either the first illumination light image or the second illumination light image is obtained as a medical image according to a light emission pattern in the mono-emission mode.

Figure 4:
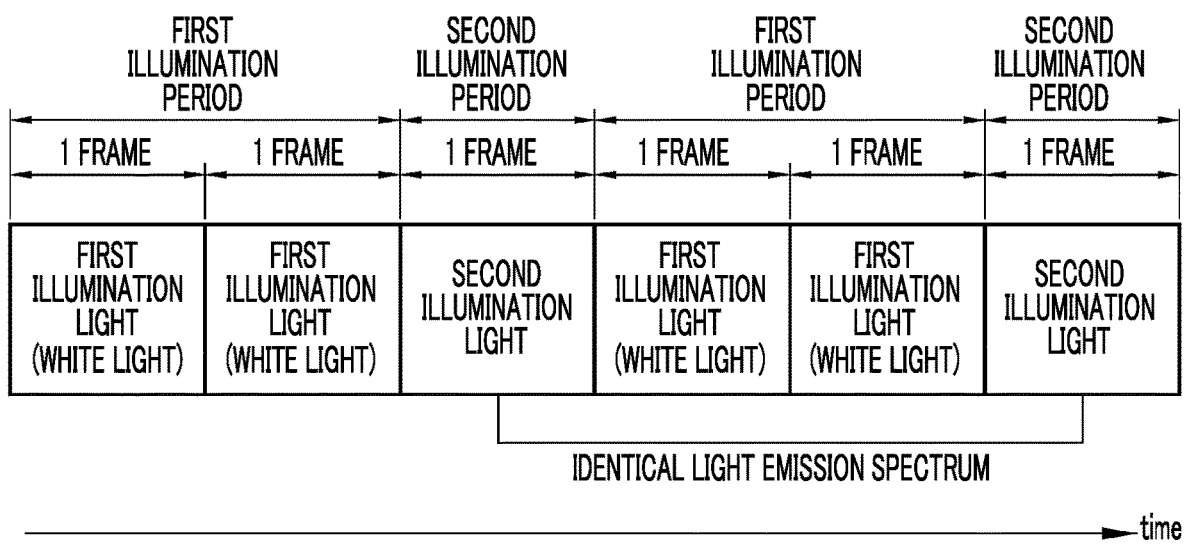
FIG. 4 is an explanatory diagram showing a first light emission pattern in an image analysis mode.
Figure 5:
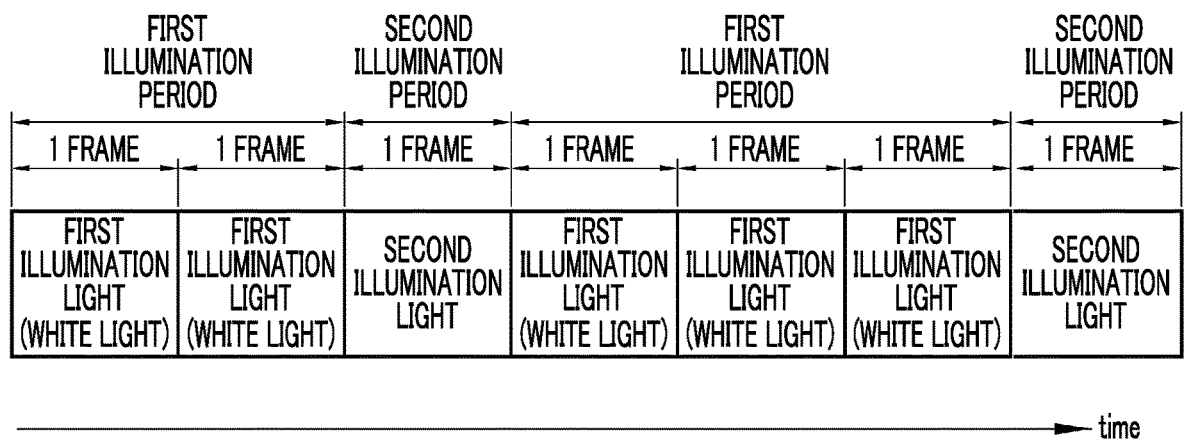
FIG. 5 is an explanatory diagram showing a second light emission pattern in the image analysis mode.

On the other hand, in the case of the multi-emission mode, control is performed such that amounts of the violet light V, the blue light B, the green light G, and the red light R are changed according to a specific pattern. For example, the first illumination light and the second illumination light are switched therebetween, as a light emission pattern, as shown in FIG. 4, as in a first light emission pattern in which the number of frames in a first illumination period in which the first illumination light illuminates a subject is the same as that in each first illumination period and, as shown in FIG. 5, a second light emission pattern in which the number of frames in the first illumination period is different from that in each first illumination period. In FIGS. 4 and 5, time represents a direction of passage of time. The frame means a time from when an image pick-up sensor (not shown) provided at the tip part 12d of the endoscope starts receiving return light from an observation target to when output of accumulated charge signals on the basis of the received light is completed. The second illumination period is a period in which the subject is illuminated by the second illumination light.

The light emitted by each of the LEDs 20a to 20d (refer to FIG. 2) is incident to a light guide 23 via an optical path coupling portion 22 configured with a mirror, a lens, and the like. The light guide 23 propagates light from the optical path coupling portion 22 to the tip part 12d of the endoscope 12.

An illumination optical system 30a and an image pick-up optical system 30b are provided at the tip part 12d of the endoscope 12. The illumination optical system 30a has an illumination lens 31, and the illumination light propagated by the light guide 23 is applied to an observation target via the illumination lens 31. In a case where the light source unit 20 is built in the tip part 12d of the endoscope 12, the light source unit 20 emits light toward a subject via the illumination lens of the illumination optical system without using the light guide. The image pick-up optical system 30b has an objective lens 41 and an image pick-up sensor 43. Light from an observation target due to the irradiation of the illumination light is incident to the image pick-up sensor 43 via the objective lens 41 and the zoom lens 42. Consequently, an image of the observation target is formed on the image pick-up sensor 43. The zoom lens 42 is a lens for enlarging the observation target, and is moved between the telephoto end and the wide end by operating the zoom operating part 12i.

The image pick-up sensor 43 is a primary color sensor, and includes three types of pixels such as a blue pixel (B pixel) having a blue color filter, a green pixel (G pixel) having a green color filter, and a red pixel (R pixel) having a red color filter.

The image pick-up sensor 43 is preferably a charge-coupled device (CCD) or a complementary metal oxide semiconductor (CMOS). The image pick-up processor 44 controls the image pick-up sensor 43. Specifically, an image signal is output from the image pick-up sensor 43 by the image pick-up processor 44 reading out a signal of the image pick-up sensor 43. The output image signal is transmitted to a medical image acquisition unit 60 of the processor device 15.

The medical image acquisition unit 60 performs various types of signal processing such as a defect correction process, an offset process, a demosaic process, a matrix process, white balance adjustment, a gamma conversion process, and a YC conversion process on the received color image. Next, image processing including a 3×3 matrix process, a gradation conversion process, a color conversion process such as three-dimensional look up table (LUT) processing, a color emphasis process, and a structure emphasis process such as spatial frequency emphasis is performed.

In the processor device 15, a first central control unit 55 configured with an image control processor operates a program in a program memory to realize a function of the medical image acquisition unit 60.

The medical image generated by the medical image acquisition unit 60 is transmitted to the medical image processing device 11. The medical image processing device 11 includes an image input unit 100, a lesion recognition unit 110, a demarcation line generation unit 120, a virtual incision line generation unit 130, a landmark setting unit 140, a landmark recording unit 160, a determined incision line changing unit 170, a display control unit 200, and a second central control unit 101 (refer to FIG. 2).

In the medical image processing device 11, the second central control unit 101 configured with an image analysis processor operates a program in a program memory to realize functions of the image input unit 100, the lesion recognition unit 110, the demarcation line generation unit 120, the virtual incision line generation unit 130, the landmark setting unit 140, the landmark recording unit 160, the determined incision line changing unit 170, and the display control unit 200.

Figure 6:
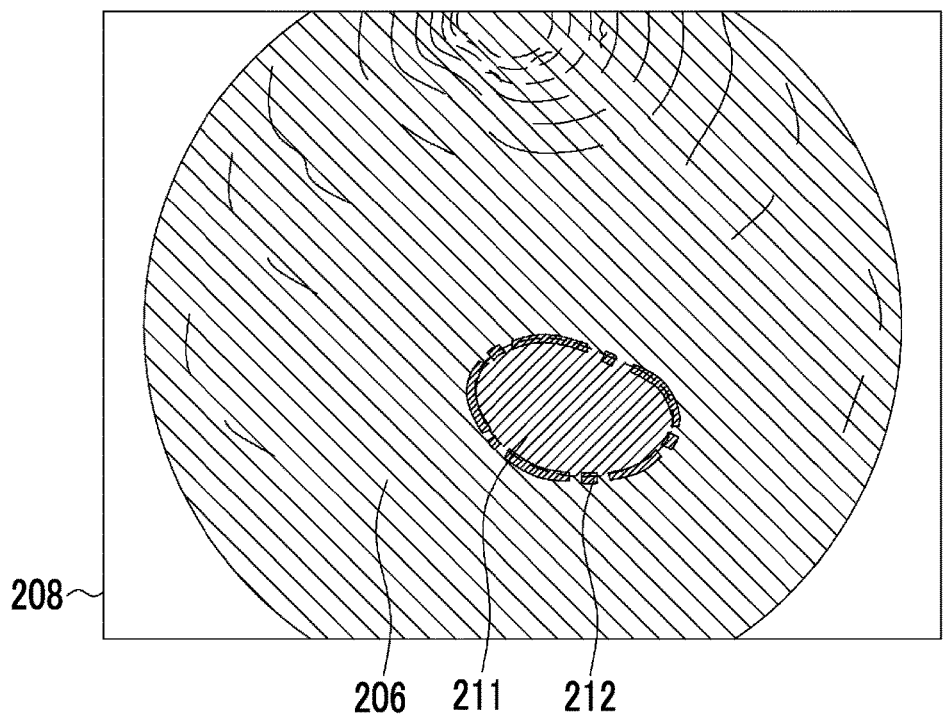
FIG. 6 is an image diagram showing an example of a medical image in which a demarcation line is generated.
Figure 7:
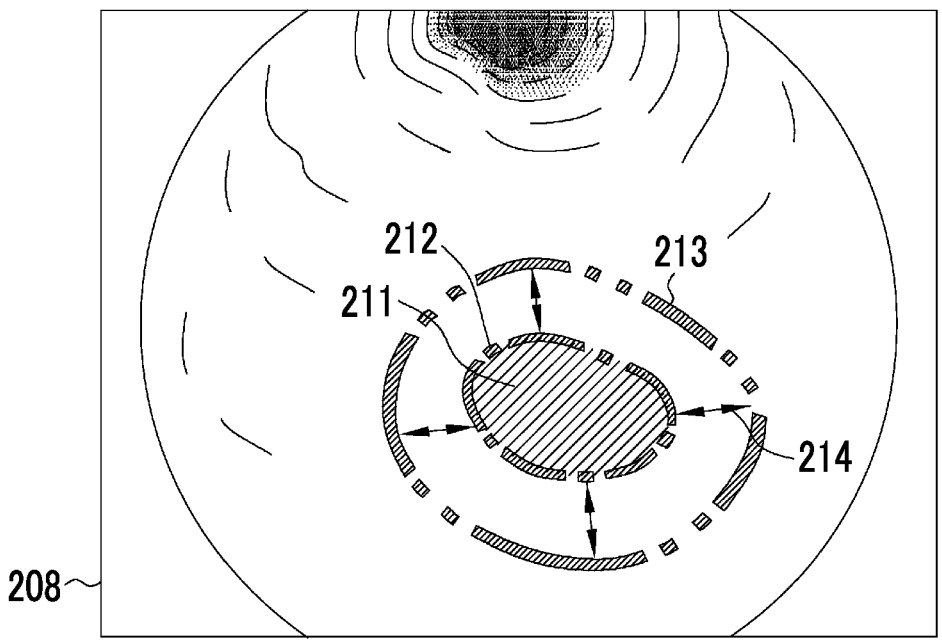
FIG. 7 is an image diagram showing an example of a display image in which a virtual incision line is displayed at a position separated from a demarcation line by a designated distance.

The medical image is transmitted to the image input unit 100 of the medical image processing device 11 (refer to FIG. 2). The image input unit 100 inputs a medical image to the lesion recognition unit 110. The lesion recognition unit 110 identifies a tumor region and a non-tumor region of a subject included in the input medical image. As shown in FIG. 6, the demarcation line generation unit 120 generates a demarcation line 212 that is a boundary line between a tumor region 211 and a non-tumor region 206 on the basis of a medical image 208 in which the tumor region 211 and the non-tumor region 206 are identified. Information regarding the demarcation line is transmitted to the virtual incision line generation unit 130, and the virtual incision line generation unit 130 generates a virtual incision line 213 that is a temporary incision line suitable for performing ESD at a position separated from the virtual incision line 213 by a designated distance 214 (indicated by an arrow in FIG. 7; in order to prevent the figure from being complicated, only one is given the reference numeral in FIG. 7) from the demarcation line 212. Information regarding the demarcation line 212 and the virtual incision line 213 is transmitted to the display control unit 200 in association with the medical image, and the display control unit 200 superimposes the demarcation line 212 and the virtual incision line 213 on the medical image, and generates a display image 210 as shown in FIG. 8 to be displayed on the display 17.

Figure 8:
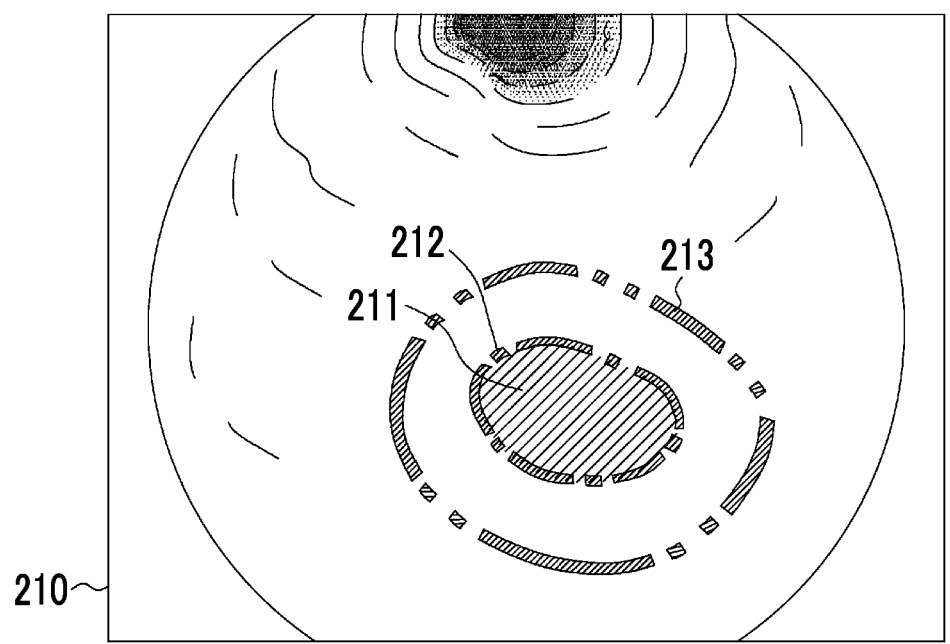
FIG. 8 is an image diagram showing an example of a display image in which a demarcation line and a virtual incision line are displayed.

A demarcation line 212 (indicated by a dot chain line in FIG. 8) that is a boundary between the tumor region 211 and the non-tumor region 206, and a virtual incision line 213 (indicated by a two-dot chain line in FIG. 8) are displayed in the display image 210 exemplified in FIG. 8. Whether or not to display the demarcation line 212 or the virtual incision line 213 in the display image 210 may be freely set.

The lesion recognition unit 110 is preferably a learning model for identifying a tumor region and a non-tumor region, which has performed learning by using training image data in which a tumor region and a non-tumor region are previously identified. Information regarding the tumor region and the non-tumor region in the training image data may be added by a skilled doctor, or may be automatically added by a device other than the medical image processing device 11. Information output by the lesion recognition unit 110 or another learning model may be added to a medical image and used for learning of the lesion recognition unit 110 as training image data.

It is preferable to use deep learning for machine learning to generate a learning model, and, for example, it is preferable to use a multi-layer convolutional neural network. In addition to the deep learning, the machine learning includes a determination tree, a support vector machine, a random forest, regression analysis, supervised learning, semi-unsupervised learning, unsupervised learning, reinforcement learning, deep reinforcement learning, learning using neural networks, a hostile generation network, and the like.

The virtual incision line is a temporary incision line suitable for performing ESD. The ESD goes through the steps of (1) marking around a tumor, (2) local injection into the submucosal layer, (3) incision of the mucous membrane, (4) peeling of the submucosal layer, and (5) hemostasis, and a malignant tumor or the like is resected under the endoscope. Before starting these procedures, a demarcation line and a virtual incision line are set and displayed such that an operator can recognize a position of a lesion and a position to be treated, and can thus assist the operator in determining a marking position, whether to perform local injection, and whether to incise the mucous membrane. Since the medical image processing device 11 generates the demarcation line and the virtual incision line on the basis of the medical image, in a case where there is a device that generates a medical image, the medical image processing device 11 is simply connected to the device. Therefore, ESD support can be performed without providing a special member or device in the endoscope 12.

It is preferable that a designated distance for generating the virtual incision line from the demarcation line is freely settable. The designated distance is preferably a distance at which the tumor region can be reliably resected and the non-tumor region is not resected too much. It is recommended that the designated distance is 5 mm in order to perform appropriate ESD, but since the designated distance may change depending on the degree of inflammation or lesion, it is preferable that the designated distance is freely settable. The subject is a luminal organ such as the esophagus, the stomach, the duodenum, the jejunum, the ileum, the cecum, the ascending colon, the transverse colon, the descending colon, the sigmoid colon, or the rectum.

The virtual incision line generation unit 130 determines the virtual incision line as a determined incision line in a case where there is an approval instruction. The approval instruction is confirmed by a user such as an operator or an assistant by viewing the display image 210 in which the virtual incision line is displayed on the display 17, and is transmitted to the medical image processing device 11 via the user interface 19 in a case where the virtual incision line is approved as an incision line for actually performing treatment. In a case where a virtual incision line is generated, an approval instruction may be automatically transmitted such that the incision line may be set to be determined as a determined incision line. Upon receiving the approval instruction, the virtual incision line generation unit 130 generates a determined incision line image in which the determined incision line is superimposed on the medical image. The display control unit 200 further superimposes the demarcation line on the determined incision line image, and generates a display image 220 to be displayed on the display 17, as shown in FIG. 9.

Figure 9:
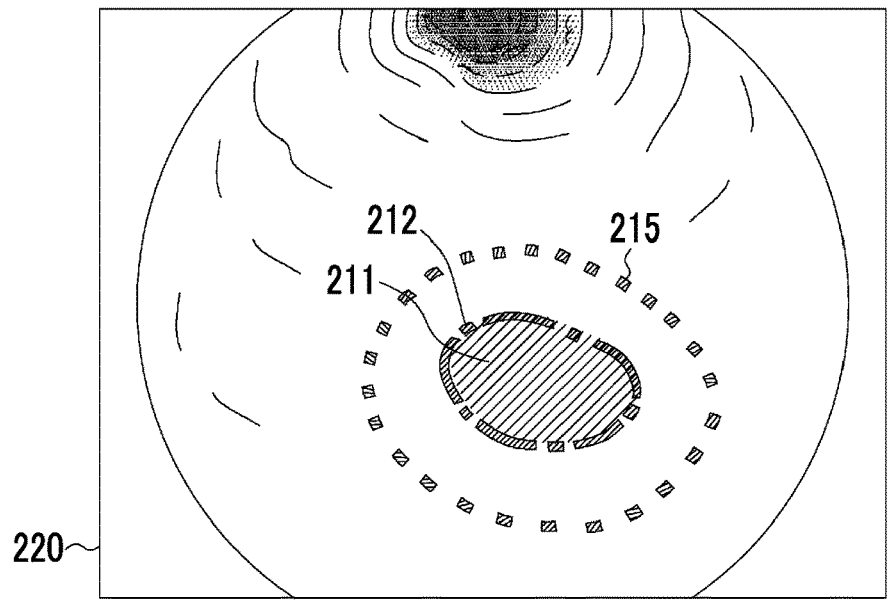
FIG. 9 is an image diagram showing an example of a display image in which a demarcation line and a determined incision line are displayed.

The display image 220 exemplified in FIG. 9 displays the tumor region 211, the demarcation line 212 (indicated by a dot chain line in FIG. 9), and the determined incision line 215 (indicated by a dot line in FIG. 9). Whether or not to display the demarcation line 212 or the determined incision line 215 in the display image 220 is freely settable.

Figure 10:
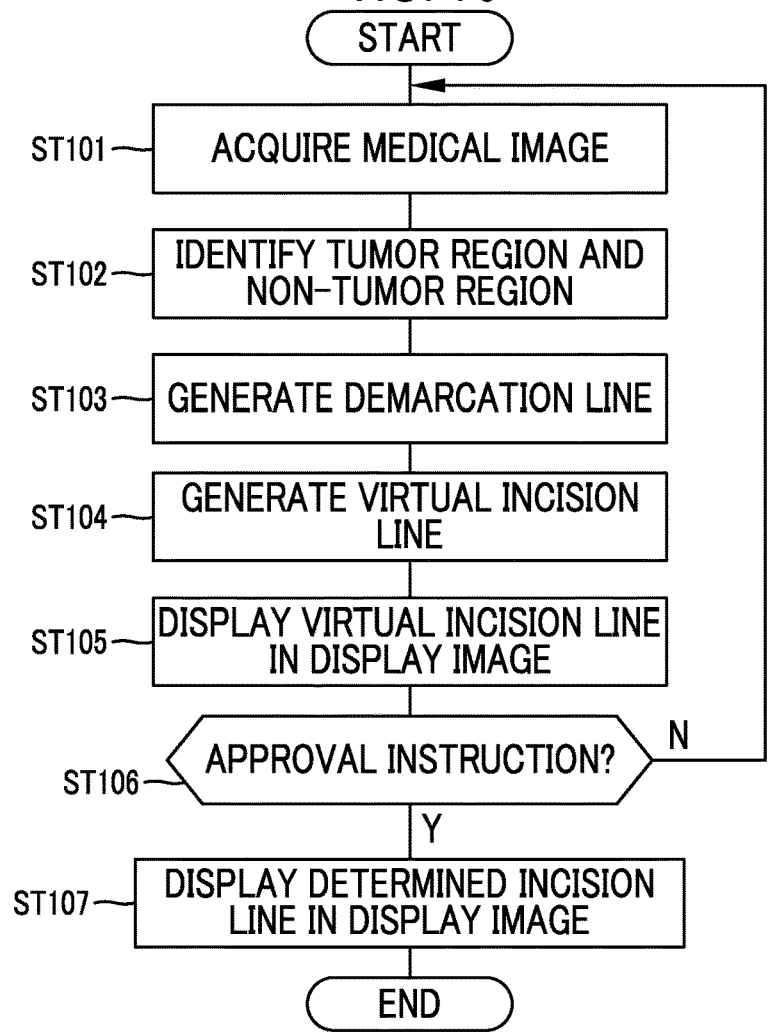
FIG. 10 is a flowchart showing a flow from acquiring a medical image to displaying a determined incision line on a display image.

A flow from acquiring a medical image to displaying a determined incision line in a display image is as shown in a flowchart of FIG. 10. The medical image processing device 11 acquires a medical image (ST101), the lesion recognition unit 110 identifies a tumor region and a non-tumor region on the medical image (ST102), the demarcation line generation unit 120 generates a demarcation line at a boundary between the tumor region and the non-tumor region (ST103), the virtual incision line generation unit 130 generates a virtual incision line at a position separated from the demarcation line by a designated distance (ST104), and the display control unit 200 generates a display image in which the demarcation line and the virtual incision line are superimposed on the medical image (ST105). In a case where an approval instruction is given, the virtual incision line generation unit 130 determines the virtual incision line as a determined incision line, generates a determined incision line image in which the determined incision line is superimposed on the medical image, and generates a display image in which the demarcation line and the determined incision line are superimposed on the medical image (ST107).

In a case where an operator moves the endoscope 12 such that the tumor region (captured in the medical image) is moved on the medical image, the determined incision line changing unit 170 preferably change a display position of the determined incision line in tracking of the tumor region. The display position of the determined incision line may be changed through image processing using artificial intelligence installed in the medical image processing device 11, or may be changed on the basis of a landmark that will be described later. The movement of the tumor region means that a subject captured in medical images acquired in chronological order changes in a time series. The change means that a position of the determined incision line superimposed on the medical image changes in a time series.

Figure 11:
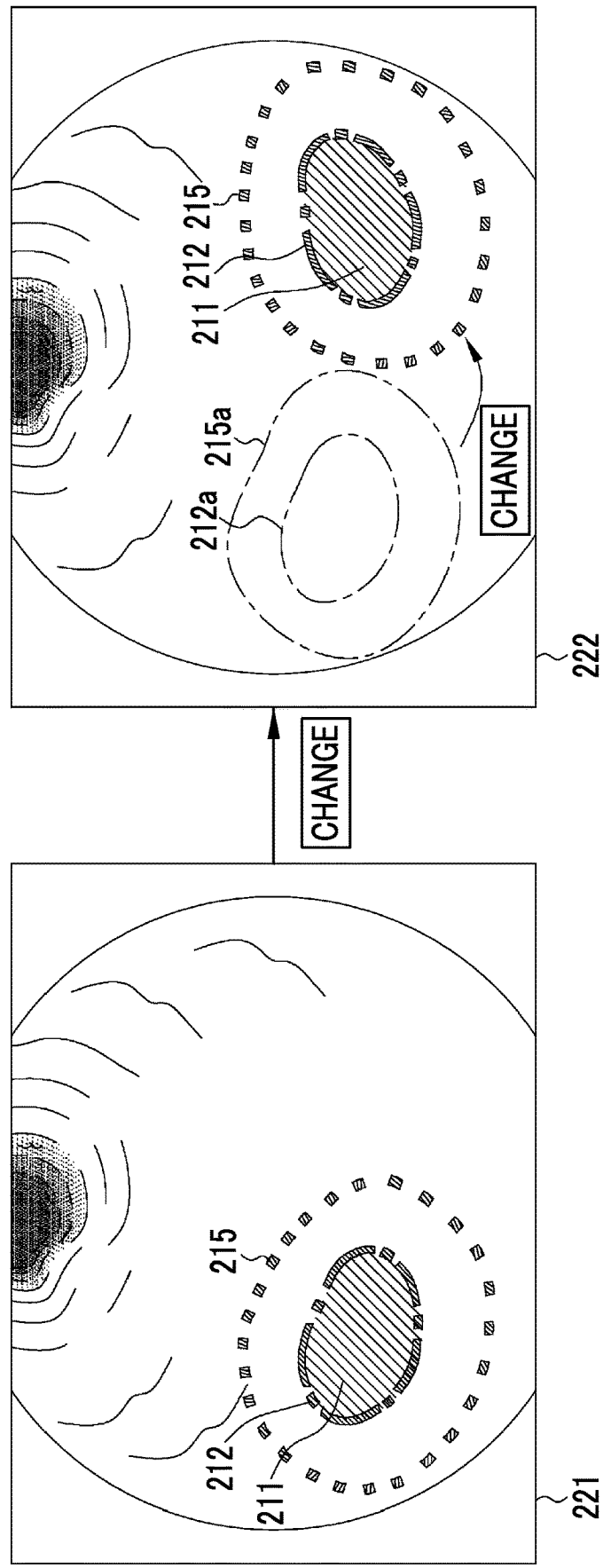
FIG. 11 is an explanatory diagram showing a change of a determined incision line in a case where a field of view is moved.

Specifically, as shown in FIG. 11, in a case where a field of view of the medical image moves from the display image 221 before movement on the left side to the display image 222 after movement on the right side and thus the tumor region 211 is moved, the determined incision line changing unit 170 changes a position of the determined incision line 215. In FIG. 11, a demarcation line 212a before movement and a determined incision line 215a before movement displayed in the display image 221 before movement on the left side are indicated by thin dot chain lines in the display image 222 after movement on the right side. With the above configuration, even in a case where the field of view moves, a user can recognize a tumor region and a portion to be incised by displaying the demarcation line and the determined incision line in tracking of the tumor region.

In a case of changing a display position of the determined incision line on the basis of a landmark, the determined incision line changing unit 170 performs a position information estimation process based on position information of the landmark, and changes a display position of the determined incision line 215 superimposed on the determined incision line image. In this case, the virtual incision line generation unit 130 transmits the determined incision line image to the landmark setting unit 140 (refer to FIG. 2), and the landmark setting unit 140 sets a landmark on the determined incision line image 141. The determined incision line 215 is associated with the landmark and is temporarily recorded in the landmark recording unit 160.

Figure 12:
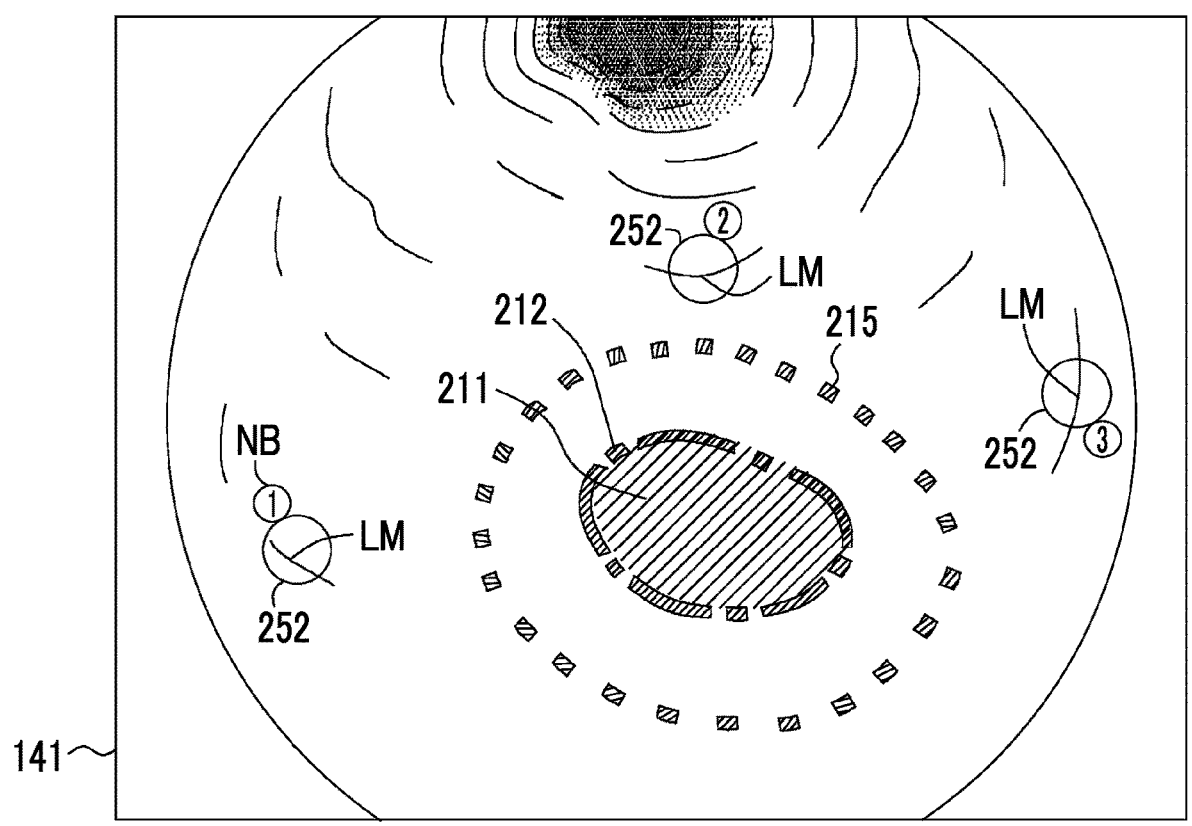
FIG. 12 is an image diagram showing a method of setting a landmark on a determined incision line image.

The landmark setting unit 140 detects a landmark LM by performing a detection process on the determined incision line image 141, and further acquires position information of the landmark LM. The landmark LM includes a blood vessel, for example, a blood vessel emphasized through drug fluorescence (photodynamic diagnosis (PDD)), a lesion part such as a tumor, or any of various structures such as glandular ductal structures. As shown in FIG. 12, in a case where a plurality of landmarks LM are detected through the detection process in the determined incision line image 141 in which the tumor region 211 is detected, the display control unit 200 performs control for a plurality of landmark position display circles 252 on the display 17 as position information of the landmarks LM. In this case, it is preferable to be able to distinguish the landmark position display circles 252 from each other. For example, each landmark position display circle 252 is given a number NB (distinction number) for distinction.

In a case where a landmark is detected through the detection process, a landmark setting process for associating the landmark position information with actual position information of a detection target is performed. As shown in FIG. 12, in the landmark setting process, as a method of associating the position information of the landmark LM with actual position information of the tumor region 211, the demarcation line 212 and the landmark position display circle 252 are connected via a link line (not shown). In this case, it is preferable to associate position information of the landmark LM detected around the tumor region C211 among the landmarks LM with actual position information of the tumor region 211. That is, in the case of FIG. 12, the landmark position display circles 252 having the distinction numbers "1", "2", and "3" around the demarcation line 212 is required to be connected to at least the demarcation line 212 via link lines. It is preferable to connect different landmark position display circles 252 via a link line. Information regarding the position information of the landmark LM and the actual position information of the detection target associated through the landmark setting process is further associated with the determined incision line and stored in the landmark recording unit 160. The information regarding the demarcation line may be associated with the information regarding the landmark and the determined incision line in the landmark recording unit 160. The landmark setting unit 140 is preferably a landmark detection learning model that has learned training image data including landmarks and is equipped with machine learning. With the above configuration, even in a case where a field of view moves, the demarcation line and the determined incision line are displayed on the basis of the landmark in tracking of movement of the landmark accompanying the movement of the subject captured in the determined incision line image, and thus a user can accurately recognize a tumor region and the portion to be incised on the basis of the position information.

Figure 13:
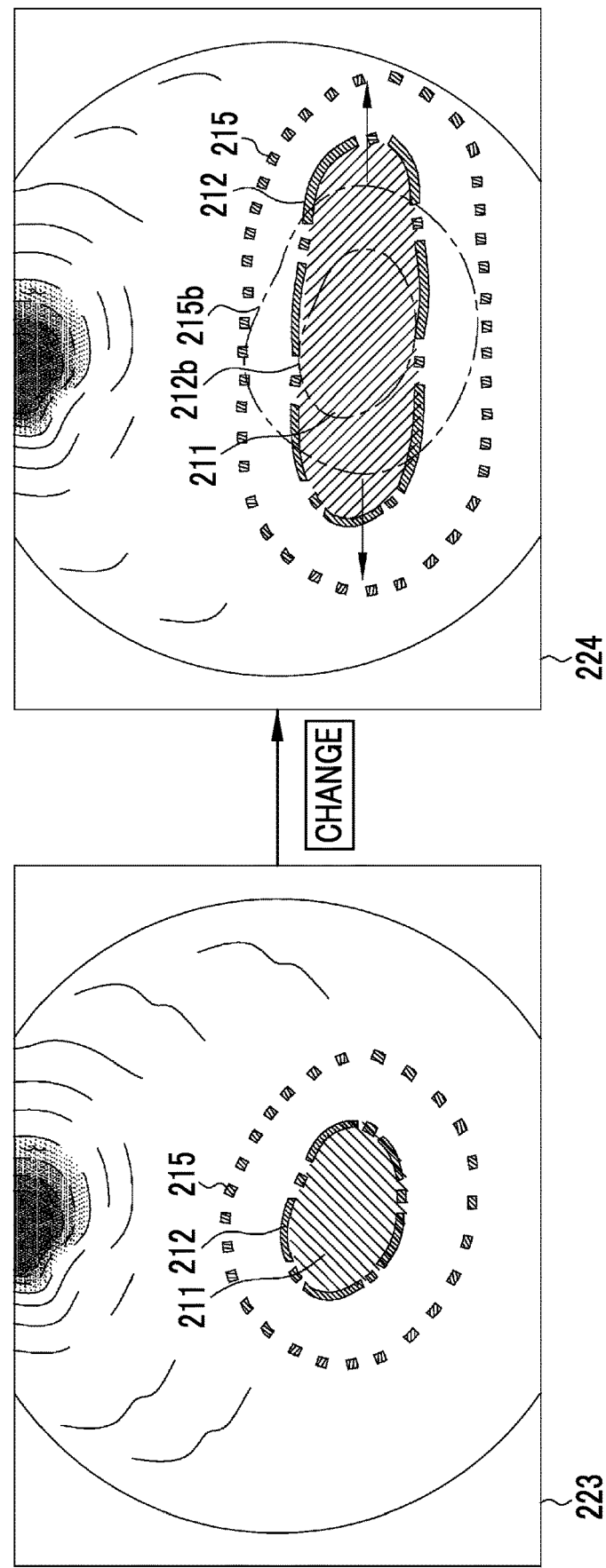
FIG. 13 is an explanatory diagram showing a change of a determined incision line in a case where an amount of gas is changed.

Other examples in which a display position of the determined incision line is changed will be described below. The determined incision line changing unit 170 may change a display position of the determined incision line according to a change in an amount of gas sent to a subject. In a case of performing ESD, a gas such as air or carbon dioxide gas may be sent into the digestive tract of the subject in order to prevent the field of view from being obstructed by structures such as folds. In this case, the mucous membrane or the tumor region 211 are stretched, and thus the appearance of the tumor region changes. A viewing angle of the tumor region 211 may change. Specifically, by injecting air as a gas, a field of view changes from the display image 223 in a case where an amount of air on the left side of FIG. 13 is small to the display image 224 in a case where an amount of air on the right side is large. In FIG. 13, the demarcation line 212*b* and the determined incision line 215*b* displayed on the display image 223 on the left side in a case where an amount of air on the right side is small are indicated by thin dot chain lines in the display image 224 on the right side in a case where an amount of air is large. The arrows indicate movement of the change of the determined incision line, that is, a relationship before and after the change of the determined incision line. In a case where a landmark is used, a display position of the determined incision line 215 is changed through a position information estimation process based on position information of the landmark (not shown). With the above configuration, positions of the demarcation line and the determined incision line can be tracked and displayed according to changes in a scene such as changes in an amount of air.

Figure 14:
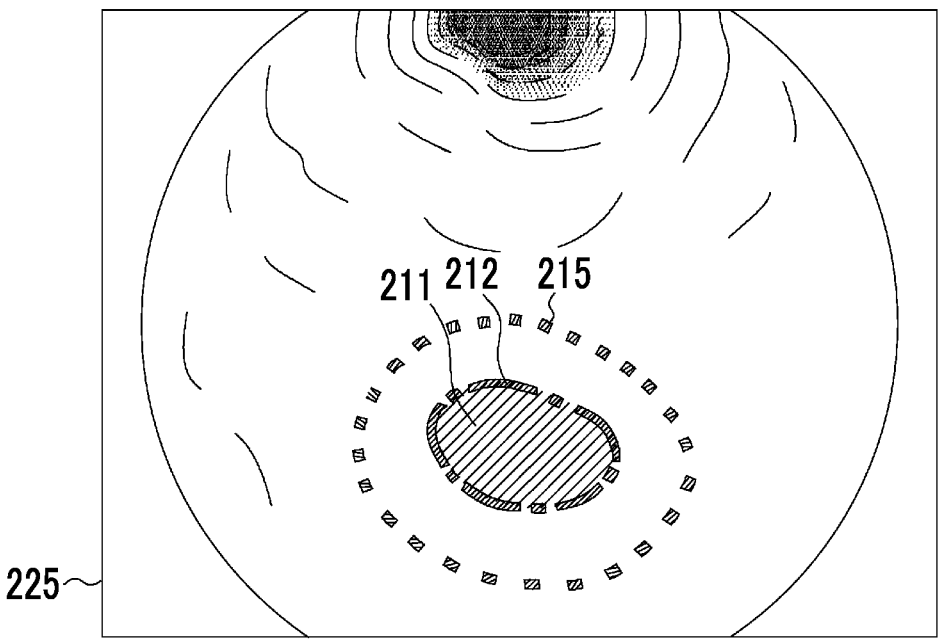
FIG. 14 is an image diagram showing an example of a low-magnification display image.
Figure 15:
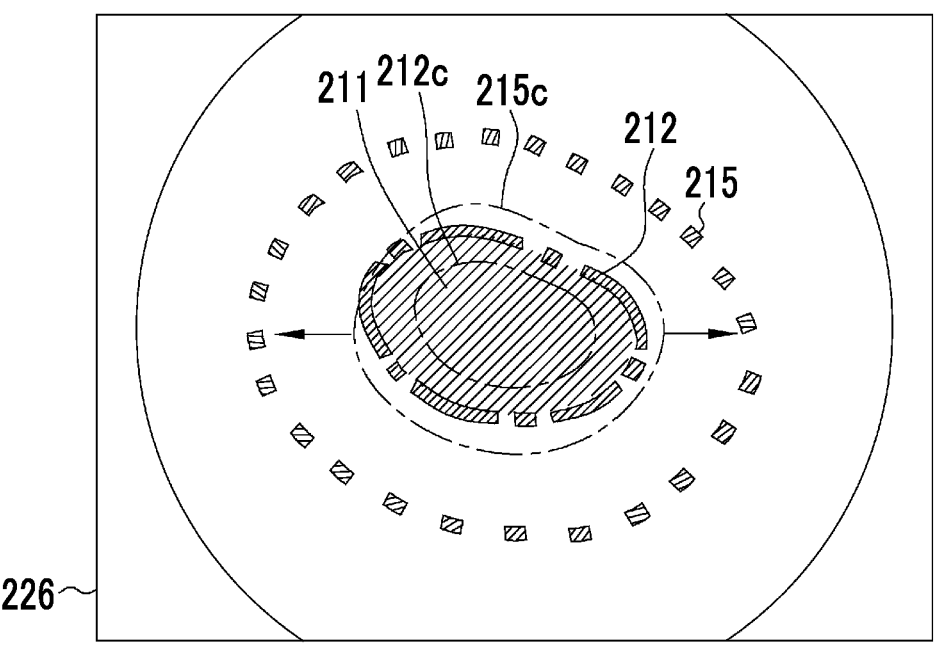
FIG. 15 is an image diagram showing a change of a determined incision line on a high-magnification display image.

The determined incision line changing unit 170 changes a display position of the determined incision line 215 according to an observation magnification of the medical image. Specifically, in a case where an observation magnification is increased as shown in FIG. 14 (low-magnification observation medical image) to FIG. 15 (high-magnification observation medical image), display positions of the demarcation line 212 and the determined incision line 215 are changed as shown in FIGS. 14 to 15. In FIG. 15, the demarcation line 212*c* and the determined incision line 215*c* displayed in the low-magnification display image 225 in FIG. 14 are indicated by thin dot chain lines in the high-magnification display image 226. The arrows indicate movement of changes of the determined incision line. In a case where a landmark is used, a display position of the determined incision line is changed through a position information estimation process based on position information of the landmark (not shown). With the above configuration, positions of the demarcation line and the determined incision line can be tracked and displayed according to changes in a scene such as the change of the magnification.

Figure 16:
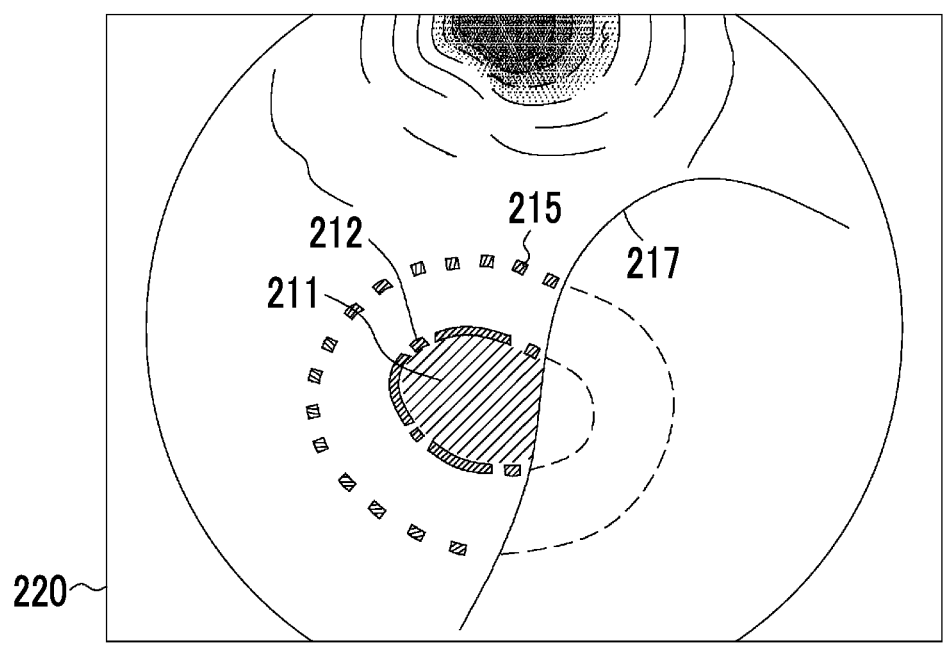
FIG. 16 is an image diagram showing a change of a determined incision line in a case where there is a bend in the mucous membrane.

The determined incision line changing unit 170 changes a display mode of the determined incision line according to a bend of the mucous membrane on the medical image. Specifically, as shown in FIG. 16, in a case where a part of the determined incision line 215 is hidden by a bend 217 of the mucous membrane captured in the medical image (the display image 220 for the determined incision line image), a display mode is changed such that parts of the demarcation line 212 and the determined incision line 215 are not displayed as shown in FIG. 16. In FIG. 16, the demarcation line 212 and the determined incision line 215 hidden by the bend 217 of the mucous membrane are indicated by thin dot lines. In a case where a landmark is used, a display position of the determined incision line is changed through a position information estimation process based on position informa-tion of the landmark (not shown). With the above configuration, in a case where positions of the demarcation line and the determined incision line are hidden by the bend of the mucous membrane, an operator can visually recognize that a site to be incised is hidden and call his/her attention. With this configuration, an operator can move the scope to a field of view in which the tumor region and the determined incision line can be seen again without losing sight of the determined incision line once set.

It is preferable that the determined incision line changing unit 170 changes a display position of the determined incision line in cooperation with the virtual incision line generation unit 130. For example, in a case where the tumor region is not included in one field of view and is cut off, and in a case where the tip part 12*d* of the endoscope 12 is moved to image the tumor region outside the field of view, it is preferable that a new virtual incision line is generated to be connected to the originally displayed determined incision line. As a specific example, a case will be exemplified in which, in the tumor region 211, a part of a first tumor portion 211*a* is displayed in a first medical image, and the other second tumor portion 211*b* (a portion that is not included in a field of view in the first medical image and is cut off) is displayed in a second medical image due to movement of the tip part 12*d*. The tumor region 211 includes the first tumor portion 211*a* and the second tumor portion 211*b*.

Figure 17:
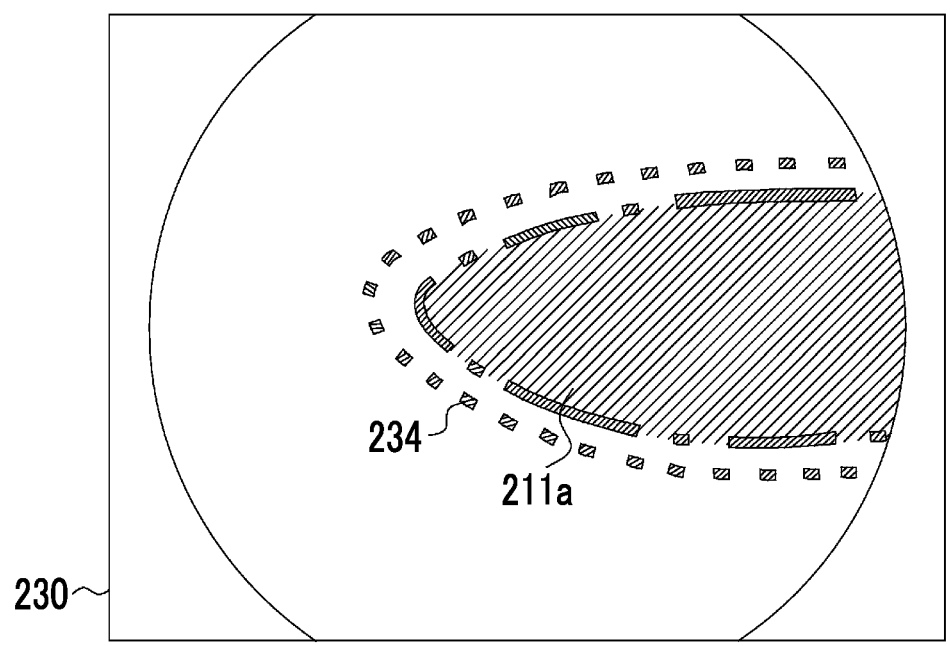
FIG. 17 is an image diagram showing an example of a first display image.

In a first display image 230 corresponding to the first medical image, as shown in FIG. 17, a demarcation line (indicated by a dot chain line) and a first virtual incision line (not shown) are generated for the first tumor portion 211*a* included in a field of view of the first medical image, and then a first determined incision line 234 (shown by a dot line in FIG. 17) is determined in response to a user's approval request. Next, the user moves the tip part 12*d* in order to display the second tumor portion 211*b* that is not indicated in the field of view of the first medical image and is cut off. In a second display image 232 corresponding to the second medical image, as shown in FIG. 18, a part of the first determined incision line 234 and the second tumor portion 211*b* that is not in the field of view in the first medical image are displayed.

Figure 18:
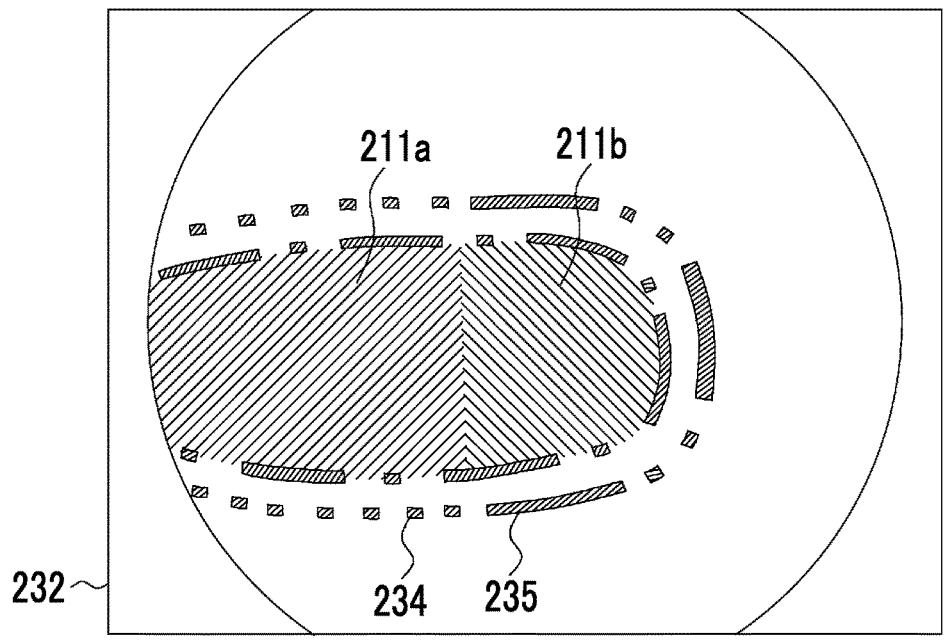
FIG. 18 is an image diagram showing a second display image in which a virtual incision line is displayed.
Figure 19:
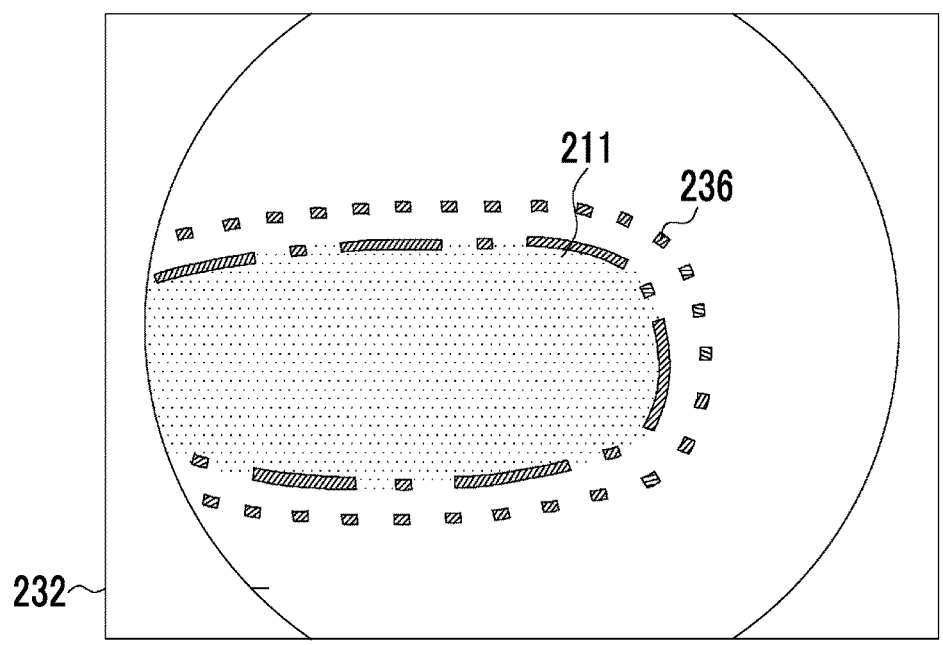
FIG. 19 is an image diagram showing a second display image in which a second determined incision line is displayed.

As shown in FIG. 18, in the second display image 232, a demarcation line (indicated by a dot chain line) and a virtual incision line 235 (indicated by a two-dot chain line in FIG. 18) are generated for the second tumor portion 211*b*. By giving the user's approval instruction in a state in which the second display image 232 is displayed, the virtual incision line 235 corresponding to the second tumor portion 211*b* is determined to be a second determined incision line, and is further connected to the first determined incision line 234, as shown in FIG. 19, to be updated to determined incision line 236 (shown by a dot line in FIG. 19) that surrounds the entire tumor region 211. The demarcation line is also generated to straddle the first medical image and the second medical image, similarly to the determined incision line 236. In a case where a landmark is used to generate the second virtual incision line, a generation position of the second virtual incision line is set through a position information estimation process based on position information of the landmark (not shown). With the above configuration, in a case where the tumor region is cut off, a determined incision line that surrounds the entire tumor region can be set by moving the scope a little, and the demarcation line and the determined incision line are displayed to an operator. In the above description, the case where the tumor region is present across the first medical image and the second medical image has been described, but in a case where the tumor region is included in three or more medical images, the present invention is also applicable to a case where there are a first medical image to an Nth medical image.

Figure 20:
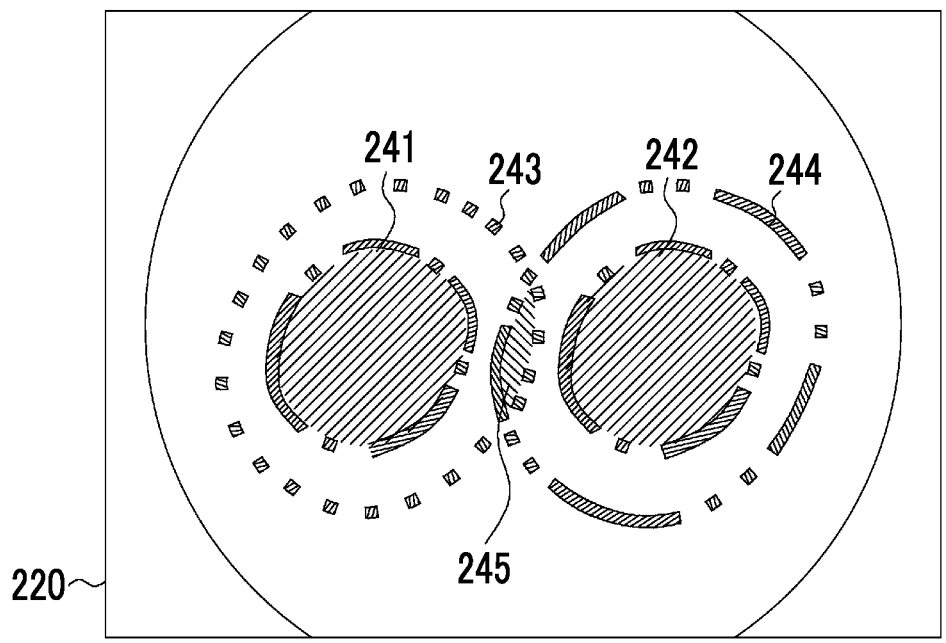
FIG. 20 is an image diagram showing a display image in which a first tumor determined incision line and a second tumor determined incision line are displayed.
Figure 21:
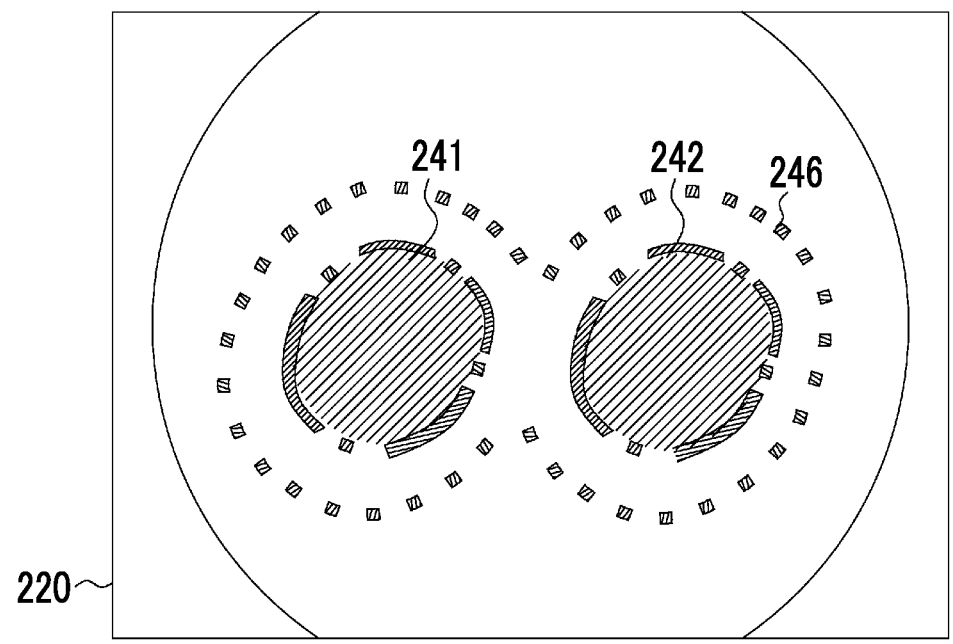
FIG. 21 is an image diagram showing a display image in which a combined incision line is displayed.

In a case where a plurality of tumor regions and determined incision lines are present in a field of view and regions surrounded by the determined incision lines overlap each other, the determined incision line changing unit 170 may set a single combined incision line by connecting the determined incision lines to each other. Specifically, as shown in FIG. 20, the display image 220 includes a first tumor region 241 and a second tumor region 242, a first tumor determined incision line 243 (indicated by a dot line in FIG. 20) corresponding to the first tumor region 241 and a second tumor determined incision line 244 (indicated by a two-dot chain line in FIG. 20) corresponding to the second tumor region 242 are set as determined incision lines, and in a case where an overlapping region 245 occurs in which a first region surrounded by the first tumor determined incision line 243 and a second region surrounded by the second tumor determined incision line 244 overlap each other, the determined incision line changing unit 170 generates a combined incision line 246 by combining first tumor determined incision line 243 surrounding the first region excluding the overlapping region 245 and the second tumor determined incision line 244 surrounding the second region excluding the overlapping region 245 as shown in FIG. 21. Generation of the combined incision line 246 may be performed in response to a request for the user's approval instruction or may be performed automatically. With the above configuration, in a case where a plurality of tumor regions are present in one screen and can be resected by one ESD, a determined incision line surrounding the plurality of tumor regions can be set, and thus a demarcation line and a more appropriate determined incision line can be displayed to an operator. In the above description, the case where the first tumor region and the second tumor region are present has been described, but in a case where the tumor region is included in three or more medical images, the present invention is also applicable to a case where there are a first tumor region to an Nth tumor region.

The determined incision line changing unit 170 may set an overlapping region as an incision impossible region. This is because, in a case where a plurality of different tumor regions are close together and a determined incision line for one tumor region included in an overlapping region includes another tumor region, the overlapping region includes the tumor region and is not suitable for incision. This is also because, although the overlapping region does not include the tumor region, in a case where the determined incision line for one tumor region is present within a designated distance to another tumor region, and the overlapping region is included in a portion where the tumor cannot be completely resected, and is not suitable for incision.

Figure 22:
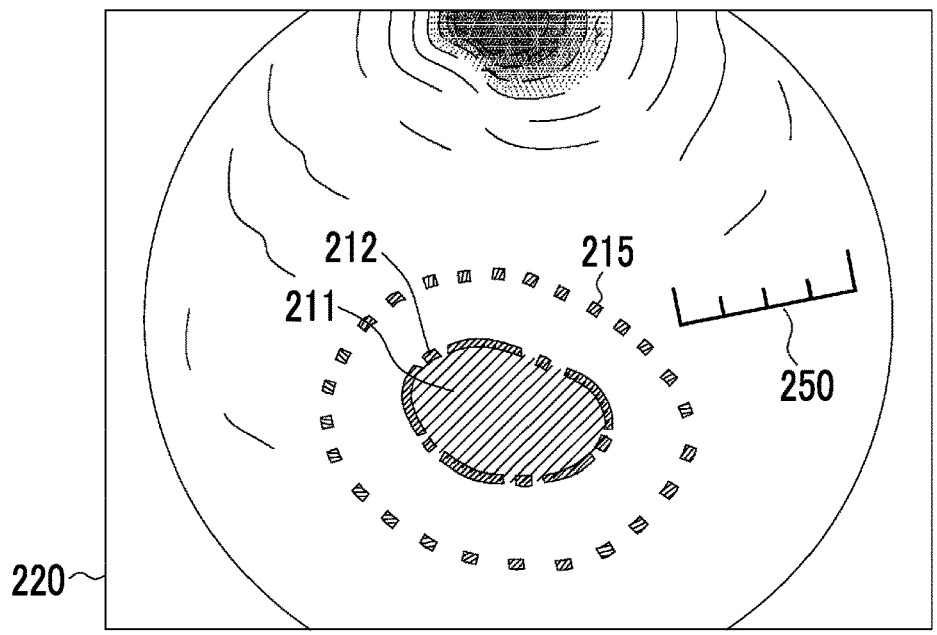
FIG. 22 is an image diagram showing a display image in which a distance measurement index is displayed.
Figure 23:
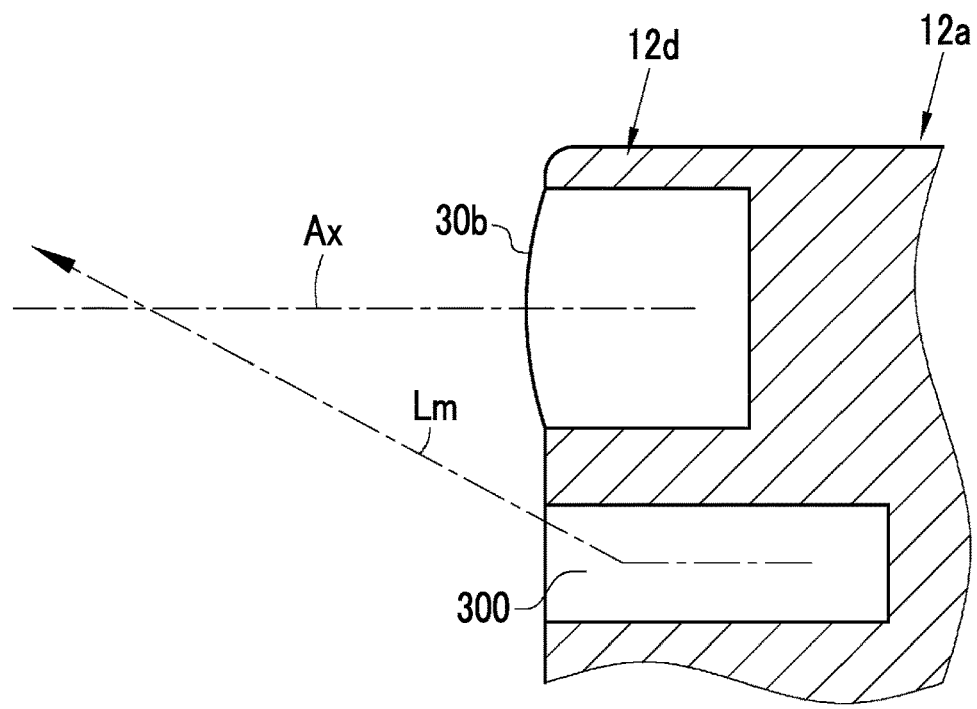
FIG. 23 is an explanatory diagram showing a distance measurement laser light emitting unit and distance measurement laser.

The lesion recognition unit 110 may measure a size of the tumor region through machine learning and set a demarcation line, or irradiate a subject with laser light, cause a distance measurement index 250 as shown in FIG. 22 to be included in a medical image, measure a size of the tumor region from the distance measurement index, and set a demarcation line. As shown in FIG. 23, distance measurement laser Lm is emitted from a distance measurement laser light emitting unit 300. In this case, the distance measurement laser Lm is applied to intersect an optical axis Ax of an image pick-up optical system 30b of the endoscope 12, and a distance (observation distance) to the scope from a subject and a size of the tumor region are measured on the basis of an irradiation position of the distance measurement laser Lm in the medical image. A size of one scale of the distance measurement index 250 depends on an irradiation distance of the laser light reflecting the distance measurement index 250, that is, an observation distance. That is, in a case where the observation distance is long, one scale of the distance measurement index 250 becomes small, and in a case where the observation distance is short, one scale of the distance measurement index 250 becomes large. By applying the distance measurement laser Lm, a size of the tumor region can be measured by using the fact that an irradiation position of the distance measurement laser Lm changes according to a change in the observation distance.

In the present embodiment, the example in which the medical image processing device 11 is connected to the endoscope system 10 has been described, but the present invention is not limited to this, and other medical devices such as an ultrasonic imaging device or a radiography device may be used. As the endoscope 12, a rigid scope or a flexible scope may be used. In the endoscope system 10, a part or the whole of the medical image acquisition unit 60 and/or the first central control unit 55 may be provided in an image processing device that communicates with, for example, the processor device 15 and cooperates with the endoscope system 10. For example, a part or the whole of the medical image acquisition unit 60 and/or the first central control unit 55 may be provided in a diagnosis support device that acquires an image picked up by the endoscope 12 directly from the endoscope system 10 or indirectly from a PACS. A part or the whole of the medical image acquisition unit 60 and/or the first central control unit 55 of the endoscope system 10 may be provided in a medical service support device including the endoscope system 10 and connected to various examination devices such as a first examination device, a second examination device, . . . , and an N-th examination device via a network.

In the present embodiment, hardware structures of processing units executing various processes, such as the medical image acquisition unit 60, image input unit 100, the lesion recognition unit 110, the demarcation line generation unit 120, the virtual incision line generation unit 130, the landmark setting unit 140, the landmark recording unit 160, the determined incision line changing unit 170, and the display control unit 200 are various processors as described below. The various processors include a programmable logic device (PLD), which is a processor of which a circuit configuration can be changed after manufacturing, such as a central processing unit (CPU) or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined. The hardware structure of the storage unit is a storage device such as a hard disk drive (HDD) or a solid state drive (SSD).

EXPLANATION OF REFERENCES

10: endoscope system
11: medical image processing device
12: endoscope
12a: insertion part
12b: operating part
12c: bendable part
12d: tip part
12e: angle knob
12f: mode selector switch
12i: zoom operating part
12j: forceps port
14: light source device
15: processor device
17: display
19: user interface
20: light source unit
20a: V-LED
20b: B-LED
20c: G-LED
20d: R-LED
21: light source processor
22: optical path coupling portion
23: light guide
30a: Illumination optical system
30b: image pick-up optical system
31: illumination lens
41: objective lens
42: zoom lens
43: image pick-up sensor
44: image pick-up processor
55: first central control unit
60: medical image acquisition unit
100: image input unit
101: second central control unit
110: lesion recognition unit
120: demarcation line generation unit
130: virtual incision line generation unit
140: landmark setting unit
141: determined incision line image
160: landmark recording unit
170: determined incision line changing unit
200: display control unit
206: non-tumor region
208: medical image
210, 220, 221, 222, 223, 224, 225, 226: display image
211: tumor region
211a: first tumor portion
211b: second tumor portion
212, 212a, 212b, 212c: demarcation line
213,235: virtual incision line
214: designated distance
215, 215a, 215b, 215c, 236: determined incision line
217: bend of mucous membrane
230: first display image
232: second display image
234: first determined incision line
241: first tumor region
242: second tumor region
243: first tumor determined incision line
244: second tumor determined incision line
245: overlapping region
246: combined incision line
250: distance measurement index
252: landmark position display circle
300: distance measurement laser light emitting unit

What is claimed is:

1. A medical image processing device comprising:
a processor configured to:
acquire a medical image obtained by imaging a subject with an endoscope;
identify a tumor region and a non-tumor region of the subject included in the acquired medical image;
generate a demarcation line that is a boundary between the tumor region and the non-tumor region on the basis of a medical image in which the tumor region and the non-tumor region are identified;
generate a virtual incision line at a position separated from the generated demarcation line by a designated distance; and
generate a display image to be displayed, by superimposing the generated demarcation line and the generated virtual incision line.

2. The medical image processing device according to claim 1, wherein
the processor is configured to determine the virtual incision line as a determined incision line in a case where an approval instruction is given.

3. The medical image processing device according to claim 2, wherein
the processor is configured to change a display position of the determined incision line in tracking of the tumor region in a case where the tumor region is moved on the medical image.

4. The medical image processing device according to claim 3, wherein
the processor is configured to:
set a landmark on a determined incision line image in which the determined incision line is superimposed on the medical image;
record the determined incision line and the landmark on the determined incision line image in association with each other; and
change the display position of the determined incision line according to movement of the landmark on the determined incision line image.

5. The medical image processing device according to claim 3, wherein
the display position of the determined incision line is changed according to a change of an amount of gas injected into the subject.

6. The medical image processing device according to claim 3, wherein
the display position of the determined incision line is changed according to a change of an observation magnification of the medical image.

7. The medical image processing device according to claim 3, wherein
a display mode of the determined incision line is changed according to a bend of a mucous membrane on the medical image.

8. The medical image processing device according to claim 2, wherein the processor is configured to update the determined incision line by connecting the first determined incision line to a second determined incision line,
in a case where the tumor region includes a first tumor portion and a second tumor portion,
the first tumor portion is displayed in a first medical image, and the second tumor portion is displayed to be included in a second medical image of which an imaging position is different from that of the first medical image, and
a part of a first determined incision line corresponding to the first tumor portion and the virtual incision line corresponding to the second tumor portion are displayed as the determined incision line in a second display image corresponding to the second medical image, and there is an approval instruction for determining the virtual incision line corresponding to the second tumor portion as the second determined incision line.

9. The medical image processing device according to claim 2, wherein
the processor is configured to generate a combined incision line by combining a first tumor determined incision line surrounding a first region excluding the overlapping region with a second tumor determined incision line surrounding a second region excluding an overlapping region,
in a case where the determined incision line includes the first tumor determined incision line corresponding to the first tumor region and the second tumor determined incision line corresponding to the second tumor region different from the first tumor region, and the overlapping region occurs in which the first region surrounded by the first tumor determined incision line and the second region surrounded by the second tumor determined incision line overlap each other.

10. The medical image processing device according to claim 9, wherein
the processor is configured to set the overlapping region as an incision impossible region.

11. The medical image processing device according to claim 1, wherein
the processor is configured to recognize a distance measurement index from the medical image and generate the demarcation line and the virtual incision line.

12. The medical image processing device according to claim 1, wherein
the designated distance is freely settable.

13. The medical image processing device according to claim 1, wherein
the subject is a luminal organ.

14. An endoscope system comprising:
the medical image processing device according to claim 1; and
the endoscope.

15. An operation method for a medical image processing device, executed by a processor, comprising:
acquiring a medical image obtained by imaging a subject with an endoscope;
identifying a tumor region and a non-tumor region of the subject included in the acquired medical image;
generating a demarcation line that is a boundary between the tumor region and the non-tumor region on the basis of a medical image in which the tumor region and the non-tumor region are identified;
generating a virtual incision line at a position separated from the generated demarcation line by a designated distance; and
generating a display image to be displayed, by superimposing the generated demarcation line and the generated virtual incision line.

* * * * *